(12) United States Patent
Georges et al.

(10) Patent No.: US 6,531,472 B2
(45) Date of Patent: Mar. 11, 2003

(54) TETRALONE DERIVATIVES

(75) Inventors: Guy Georges, Habach (DE); Adelbert Grossmann, Eglfing (DE); Tim Sattelkau, Mannheim (DE); Wolfgang Schaefer, Mannheim (DE); Ulrich Tibes, Frankfurt (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/006,173

(22) Filed: Dec. 4, 2001

(65) Prior Publication Data

US 2002/0065282 A1 May 30, 2002

(30) Foreign Application Priority Data

Dec. 7, 2000 (EP) ............................................ 00126820

(51) Int. Cl.⁷ ....................... A61K 31/40; A61K 31/165; C07D 207/30; C07D 211/06; C07D 265/30
(52) U.S. Cl. .................... 514/238.2; 514/319; 514/427; 514/617; 544/107; 546/206; 548/560; 564/172
(58) Field of Search .............................. 514/238.2, 319, 514/427, 617; 544/107; 546/206; 548/560; 564/172

(56) References Cited

U.S. PATENT DOCUMENTS 5,369,108 A 11/1994 Breslow et al.

FOREIGN PATENT DOCUMENTS

WO  WO 98/55449  12/1998

Primary Examiner—Taofiq Solola
(74) Attorney, Agent, or Firm—George W. Johnston; Patricia S. Rocha-Tramaloni; Eileen M. Ebel

(57) ABSTRACT

The present invention provides compounds of formula I

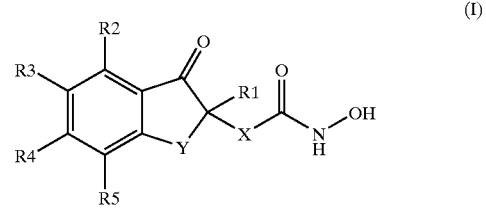

and pharmaceutically acceptable salts, wherein R1, R2, R3, R4, R5, X and Y have the meanings defined in the specification. The compounds have histone deacetylase (HDAC) inhibitory activity which is useful in cancer treatment. Also provided is a process for making a compound of formula I by reacting a compound of formula III

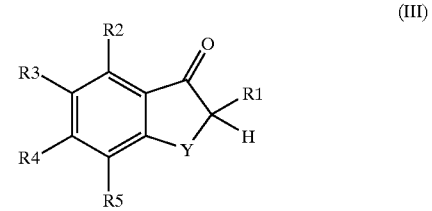

with a compound of formula IV

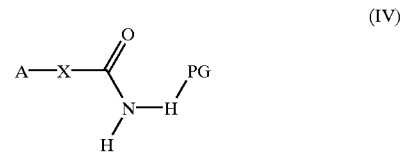

wherein
A is a displaceable group and PG is a protecting group.

8 Claims, No Drawings

TETRALONE DERIVATIVES

BACKGROUND OF THE INVENTION

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating an accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis.

Several structural classes of HDAC inhibitors are described in the state of the art and were reviewed by Marks, P. M., et al., J. Natl. Cancer Inst. 15 (2000) 1210–1216. Hydroxamic acid compounds having HDAC inhibitory activity are also described in WO 98/55449 and U.S. Pat. No. 5,369,108.

Suberoylanilide hydroxamine acid (SAHA) was shown to have HDAC inhibitory activity as indicated in U.S. Pat. No. 5,369,108.

SUMMARY OF THE INVENTION

The present invention relates to (1-oxo-1,2,3,4-tetrahydro-naphthalen-2-yl)-alkanoic acid hydroxamides. These compounds possess anti-cell proliferation activity such as anti-cancer activity.

The present invention provides a compound selected from compounds of formula I

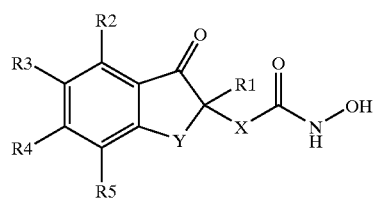

(I)

wherein:
R1 is selected from hydrogen, (1-4C)alkyl, COOH, and COO(1-4C)alkyl;
R2, R3, R4, R5 are independently selected from hydrogen, a halogen atom, an (1-4C)alkyl-, trifluoromethyl-, hydroxy-, (1-4C)alkoxy-, aryloxy-, arylalkyloxy-, nitro-, amino-, (1-4C)alkylamino-, di[(1-4C)alkyl]-amino-, piperidino, morpholino, pyrrolidino, (1-4C)alkanoylamino-, an aryl group, and a heteroaryl group, or R2 and R3 together or R3 and R4 together or R4 and R5 together, respectively, can form an (1-3C)alkylenedioxy ring, or R2 and R3 together or R3 and R4 together or R4 and R5 together, respectively, can form an (3-5C)alkylene chain;
Y is —CH2—CH2—;
X is an alkylene chain of 4 to 10 carbon atoms which can be saturated or unsaturated with one or two double bonds or one or two triple bonds or a one double and one triple bond, and which can be branched or unbranched or interrupted by a (3-7C) cycloalkyl ring;
and pharmaceutically acceptable salts thereof.

The present invention also provides a process for making a compound of formula I by reacting a compound of formula III

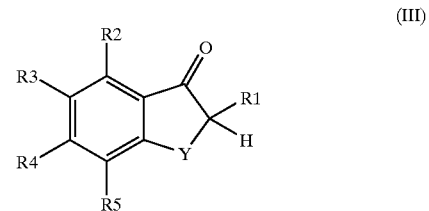

(III)

with a compound of formula IV

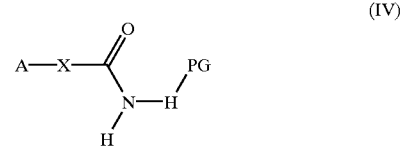

(IV)

wherein
A is a displaceable group and PG is a protecting group.

DETAILED DESCRIPTION OF THE INVENTION

It has now been found that (1-oxo-1,2,3,4-tetrahydro-naphthalen-2-yl)-alkanoic acid hydroxamides possess anti-cell-proliferation properties which arise from their HDAC inhibitory activity. The HDAC inhibitory activity of several (1-oxo-1,2,3,4-tetrahydro-naphthalen-2-yl) -alkanoic acid hydroxamides of the present invention are shown to be superior to SAHA (suberoylanilide hydroxamic acid), in their HDAC inhibitory activity.

The present invention relates to new compounds of the general formula (I) and their use as antitumor agents:

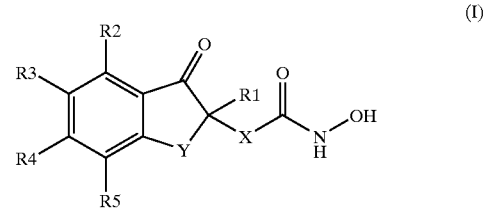

(I)

wherein:
R1 is selected from hydrogen, (1-4C)alkyl, COOH, COO(1-4C)alkyl;
R2, R3, R4, R5 are independently selected from hydrogen, a halogen atom, an (1-4C)alkyl-, trifluoromethyl-, hydroxy-, (1-4C)alkoxy-, aryloxy-, arylalkyloxy-, nitro-, amino-, (1-4C)alkylamino-, di[(1-4C)alkyl]-amino-, piperidino, morpholino, pyrrolidino, (1-4C)alkanoylamino-, an aryl group, and a heteroaryl group, or R2 and R3 together or R3 and R4 together or R4 and R5 together, respectively, form an (1-3C)alkylenedioxy ring, or R2 and R3 together or R3 and R4 together or R4 and R5 together, respectively, form an (3-5C)alkylene chain;

Y is —CH$_2$—CH$_2$—;

X is an alkylene chain of 4 to 10 carbon atoms which can be saturated or unsaturated with one or two double bonds or one or two triple bonds or one double and one triple bond, and which can be branched or unbranched or interrupted by a (3-7C) cycoalkyl ring.

The enantiomers of the compounds of formula (I), their diastereoisomers, racemates and mixtures thereof are also included in the present invention, as well as pharmaceutically acceptable salts of the compounds of formula (I) which may be salts formed from contact with pharmaceutically acceptable acids and/or bases.

It is also to be understood that certain derivatives of the formula I can exist in solvated as well as unsolvated forms such as, for example, hydrated forms. It is to be understood that the invention encompasses all such solvated forms which possess anticancer activity. Preferred compounds of formula (I) are those in which R2 and R5 are hydrogen. Particularly preferred compounds of formula (I) are those in which three out of the four radicals R2, R3, R4 and R5 are hydrogen.

A suitable value for a substituent when it is a halogen atom is, for example, fluoro, chloro, bromo and iodo; when it is (1-4C)alkyl is, for example, methyl, ethyl, propyl, isopropyl, butyl, isobutyl, sec-butyl; when it is (1-4C)alkoxy is, for example, methoxy, ethoxy, propoxy, isopropoxy or butoxy; when it is (1-4C)alkylamino is, for example, methylamino, ethylamino or isopropylamino; when it is di-[(1-4C)alkyl]amino is, for example, dimethylamino, N-ethyl-N-methylamino, diethylamino, N-methyl-N-propylamino or dipropylamino; when it is (1-4C) alkanoylamino is, for example, formylamido, acetamido, propionamido or butyramido; when it is (1-3C) alkylenedioxy is, for example, methylenedioxy, ethylenedioxy or propylenedioxy.

An aryl group is a carbocyclic conjugated ring system, for example, phenyl, naphthyl, preferably phenyl, which may be unsubstituted or substituted by 1, 2, or 3 substituents independently selected from a halogen atom, an (1-4C)alkyl-, trifluoromethyl-, hydroxy-, (1-4C)alkoxy-, arylalkyloxy-, aryloxy, (1-3C)alkylenedioxy-, nitro-, amino-, (1-4C) alkylamino-, di[(1-4C)alkyl]amino-, and an (1-4C) alkanoylamino-group as defined above.

A heteroaryl group is either a 5 or 6 membered cyclic conjugated ring system with one or two hetero atoms independently chosen from nitrogen, oxygen, and sulfur, for example pyridinyl, thiophenyl, furyl or pyrrolyl, or an anulated bicyclic conjugated ring system like indolyl-, quinolyl- or isoquinolyl-, which may be unsubstituted or substituted by 1, 2, or 3 substituents independently selected from a halogen atom, an (1-4C)alkyl-, trifluoromethylhydroxy-, (1-4C)alkoxy-, arylalkyloxy-, aryloxy, (1-3C) alkylenedioxy-, nitro-, amino-, (1-4C)alkylamino-, di[(1-4C)alkyl]amino-, and an (1-4C)alkanoylamino-group as defined above.

A preferred value for the arylalkyloxy- radical is benzyloxy.

A preferred (3-7C) cycloalkyl ring is cyclopropyl or cyclobutyl whereby the ring is bound to the chain in a 1,1'-connection.

Preferred values for the chain X are —(CH$_2$)$_n$— and —CH=CH—(CH$_2$)$_{n-2}$—, in which n is an integer from 3 to 7, most preferably from 4 to 6. Other preferred values are —(CH$_2$)$_{n-1}$—CH(CH$_3$)—, —(CH$_2$)$_{n-1}$—C(CH$_3$)$_2$— and —(CH$_2$)$_{n-1}$—C(—CH$_2$.CH$_2$—)—, in which n is an integer from 3 to 7, most preferably from 4 to 6.

According to a further aspect of the invention there is provided a pharmaceutical composition which comprises a pharmaceutically effective amount of one or more compounds of formula I or a pharmaceutically-acceptable salt thereof, as defined hereinbefore in association with a pharmaceutically-acceptable diluent, excipient or carrier. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a manner using conventional excipients.

These pharmaceutical compositions can be administered orally, for example in the form of tablets, coated tablets, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, their diastereomers, racemates, mixtures, and the salts thereof may be manufactured in a manner that is known in the art, e.g., by means of conventional mixing, encapsulating, dissolving, granulating, emulsifying, entrapping, coated tablet-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid poll. Depending on the nature of the active substance, carriers are generally not required in the case of soft gelatin capsules. Suitable carriers for the manufacture of solutions and syrups are water, polyols, saccharose, invert sugar and glucose. Suitable carriers for injection are water, alcohols, polyols, glycerin, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The (1-oxo-1,2,3,4-tetrahydro-naphthalen-2-yl)-alkanoic acid hydroxamide will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example, 1–250 mg of active ingredient. Preferably a daily dose in the range of 1–100 mg/kg is employed. However the daily dose will necessarily be varied depending upon the host treated, the particular route of administration, and the severity of the illness being treated. Accordingly, the optimum dosage may be determined by the practitioner who is treating any particular patient.

According to a further aspect of the present invention there is provided a (1-oxo-1,2,3,4-tetrahydro-naphthalen-2-yl)-alkanoic acid hydroxamide derivative of the formula I as defined hereinbefore for use in a method of treatment of the human or animal body by therapy. We have now found that the compounds of the present invention possess anti-cell-proliferation properties arising from their histone deacetylase inhibitory activity. Accordingly the compounds of the present invention are useful in a method for treating the proliferation of malignant cells. Accordingly, the compounds of the present invention are expected to be useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

Thus according to this aspect of the invention there is provided the use of a (1-oxo-1,2,3,4-tetrahydro-naphthalen-2-yl)-alkanoic acid hydroxamide derivative of the formula I, or a pharmaceutically-acceptable salt thereof, as defined herein in the manufacture of a medicament for use in the production of an anti-cell-proliferation effect in a warm-blooded animal such as a human being.

According to a further feature of this aspect of the invention there is provided a method for producing an anti-cell-proliferation effect in a warm-blooded animal, such as man, in need of such treatment which comprises administering to said animal an effective amount of a (1-oxo-1,2,3,4-tetrahydro-naphthalen-2-yl)-alkanoic acid hydroxamide derivative as defined hereinbefore.

The anti-cell-proliferation treatment defined hereinbefore may be applied as a sole therapy or may involve, in addition to the (1-oxo-1,2,3,4-tetrahydro-naphthalen-2-yl)-alkanoic acid hydroxamide derivative of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitor, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl)propionanilide, or other therapeutic agents and principles as described in, for example, Cancer: Principles & Practice of Oncology, Vincent T. DeVita, Jr., Samuel Hellmann, Steven A. Rosenberg; 5$^{th}$ Ed., Lippincott-Raven Publishers (1997). Such conjoint treatment may be achieved by way of the simultaneous, sequential or separate dosing of individual components of the treatment. According to this aspect of the invention there is provided a pharmaceutical product comprising a (1-oxo-1,2,3,4,-tetrahydro-naphthalen-2-yl)-alkanoic acid hydroxamide derivative of the formula I as defined hereinbefore and an additional anti-tumor substance as defined hereinbefore for the conjoint treatment of cancer. Examples for physiologically acceptable salts of compounds of formula I are salts with physiologically acceptable bases. These salts can be, among others, alkali, earth alkali, ammonium and alkylammonium salts, for example sodium, potassium, calcium, tetramethylammonium salts.

The separation of racemic compounds into their enantiomeres can be performed by chromatography on an analytical, semipreparative or preparative scale using suitable optically active stationary phases with suitable eluents. Suitable optically active stationary phases include, but are not limited to, silica (e.g. ChiraSper™, Merck; Chiralpak™ OT/OP, Baker), cellulose esters or carbamates (e.g. Chiracel™ OB/OY, Baker) or others (e.g. Crownpak™, Daicel™ or Chiracel™ OJ-R, Baker). Other methods for the separation of enantiomers can also be applied, like the formation of diastereomeric compounds from compounds of the formula I together with other optically active compounds, e.g. camphersulfonic acid or brucin, and separation of these diastereomeric compounds, followed by the liberation from the optically active agent. Enantiomerically enriched or pure compounds of formula I are also obtainable by the usage of optically active starting materials. The compounds of the present invention encompass enantiomers, diastereoisomers and racemates of the compounds of formula I.

The compounds of formula (I) can be prepared by known methods as described in the literature (e.g., in standard textbooks such as Houben-Weyl, "Methoden der Organischen Chemie, Georg Thieme Verlag", Stuttgart; Organic Reactions, John Wiley & Sons, Inc., New York) and in the references cited in the examples and namely under reaction conditions that are known and suitable for the said reactions. One can also use known variants that are not mentioned here in detail. Compounds of formula (I) can be prepared by any process known to be applicable to the preparation of chemically related compounds. Furthermore, a compound of formula (I) can be converted by known methods into another compound of formula (I).

Such processes, when used to prepare a (1-oxo-1,2,3,4-tetrahydro-naphthalen-2-yl)-alkanoic acid hydroxamide derivative of the formula I, or a pharmaceutically-acceptable salt thereof, are provided as a further feature of the invention and are illustrated by the following representative examples in which, unless otherwise stated, X, Y, R1, R2, R3, R4, R5 and n have the meanings defined hereinbefore. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skills of an organic chemist.

(A) One preferred method for the preparation of compounds of the formula I is the deprotection of compounds of the formula II

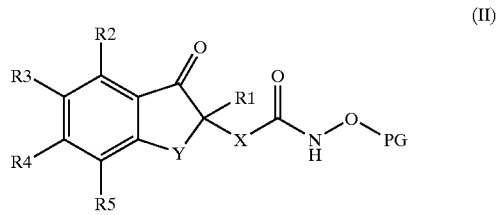

(II)

wherein PG is a suitable protecting group and in which R1, R2, R3, R4, R5, X and Y have the above meaning.

Compounds of the formula (II) are new and included in the present invention. Suitable protecting groups PG are for example the benzyl-, p-methoxybenzyl-, tert.butyloxycarbonyl-, trityl-, or silyl groups such as the trimethylsilyl- or dimethyl-tert.butylsilyl-group. The reaction conditions for the deprotection depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium or platinum on a suitable carrier such as carbon, barium sulfate, or barium carbonate, at ambient temperature and pressure. When the protecting group is a tert.butyloxycarbonyl- or a trityl group, the reaction is carried out in the presence of acids at a temperature between −20° C. to 60° C., preferably between 0° C. and ambient temperature. The acid may be a solution of hydrochloric acid in an inert solvent such as diethyl ether or dioxane, or trifluoroacetic acid in dichloromethane. When the protecting group is a silyl group such as the trimethylsilyl- or dimethyl-tert.butylsilyl-group, the reaction is preferably carried out in the presence of a fluoride source such as sodium fluoride or tetrabutyl ammonium fluoride in an inert solvent such as dichloromethane.

Compounds of the formula (II) in which R1 is COOH can be prepared from compounds of the formula (II) in which R1 is COO(1-4C)alkyl by hydrolysis of the ester moiety. The reactions carried out to achieve this transformation depend on the type of the (1-4C)alkyl-group. When the (1-4C)alkyl-group is a methyl or ethyl group, the reaction is carried out in the presence of a base, for example, lithium hydroxide, sodium hydroxide, or potassium hydroxide in an inert solvent or diluent, for example, in methanol or ethanol or tetrahydrofurane. When the (1-4C)alkyl-group is the tert-.butyl group, the reaction is carried out in the presence of an acid, for example, a solution of hydrochloric acid in an inert solvent such as diethyl ether or dioxane, or trifluoroacetic acid in dichloromethane.

Compounds of the formula (II) in which R1 is H can be prepared from compounds of the formula (II) in which R1 is COOH by thermal decarboxylation. This can be achieved by heating in an inert solvent for 1 to 48 h, preferably 5 to 9 h at a temperature between 60 and 200° C., preferably between 80 and 120° C.

Compounds of the formula (II) in which R1 is (1-4C)alkyl or COO(1-4C)alkyl can be obtained by the reaction of a compound of the formula (III)

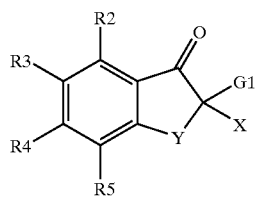

(III)

in which R2, R3, R4, R5 and Y have the above meaning, and G1 is (1-4C)alkyl or COO(1-4C)alkyl, with a compound of formula (IV)

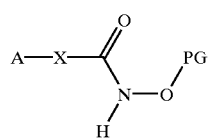

(IV)

wherein A is a displaceable group, PG has the meaning defined hereinbefore, and X has the above meaning in the absence or presence of a suitable base.

A suitable displaceable group A is, for example, a halogeno, or sulphonyloxy group, for example a chloro, bromo, methanesulphonyloxy or toluene-p-sulphonyloxy group. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofurane or 1,4-dioxane, an aromatic solvent such as toluene, or a dipolar aprotic solvent such as N,N-dimethylformamide, N,N-dimethylacetamide, N-ethylpyrrolidin-2-one or dimethylsulphoxide. The reaction is conveniently carried out at a temperature in the range, for example, 10 to 250° C., preferably in the range 50–150° C.

Compounds of the formula (II) in which R1 is hydrogen, (1-4C)alkyl or COO(1-4C)alkyl can also be obtained by the reaction of a compound of the formula (V)

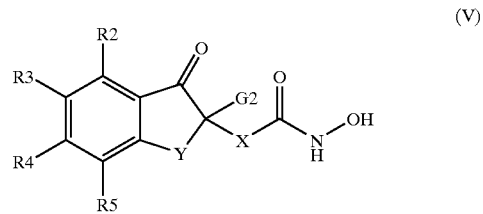

(V)

in which R2, R3, R4, R5, X and Y have the above meaning, and G2 is hydrogen, (1-4C)alkyl or COO(1-4C)alkyl

(VI)

with a compound of the formula (VI) wherein PG is a suitable protecting group as described above. This reaction typically involves a two-step one-pot procedure. In the first step, the carboxylate of the formula (V) becomes activated. This reaction is carried out in an inert solvent or diluent, for example, in dichloromethane, dioxane, or tetrahydrofurane, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. "Methoden der organischen Chemie (Houben-Weyl)" Vol. XV/1 and XV/2 are also applicable.

Compounds of the formula (V) are prepared from compounds of the formula (VII)

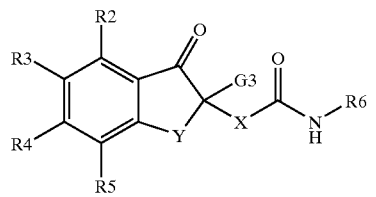

(VII)

wherein X, Y, R2, R3, R4 and R5 have the meaning defined hereinbefore and G3 is hydrogen or (1-4C)alkyl and R6 is an alkyl group, for example, a methyl, ethyl, or tert. butyl group or benzyl group, by hydrolysis. The conditions under which the hydrolysis is carried out depend on the nature of the group R6. When R6 is a methyl or ethyl group, the reaction is carried out in the presence of a base, for example, lithium hydroxide, sodium hydroxide, or potassium hydroxide in an inert solvent or diluent, for example, in methanol or ethanol. When R6 is the tert.butyl group, the reaction is carried out in the presence of an acid, for example, a solution of hydrochloric acid in an inert solvent such as diethyl ether or dioxane, or trifluoroacetic acid in dichloromethane. When R6 is the benzyl group, the reaction is carried out by hydrogenolysis in the presence of a noble metal catalyst such as palladium or platinum on a suitable carrier, such as carbon.

Compounds of the formula (VII) are prepared from compounds of the formula (VIII)

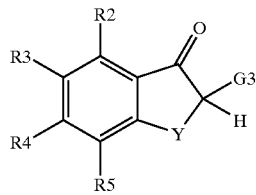

(VIII)

in which R2, R3, R4, R5, Y and G3 have the meaning defined herein above, by reaction with compounds of the formula (IX)

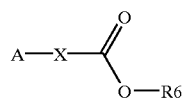

(IX)

wherein A, X and R6 have the meaning defined hereinbefore, in the absence or presence of a suitable base. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or a hydride, for example sodium hydride.

The reaction is conveniently carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofurane or 1,4-dioxane, an aromatic solvent such as toluene, or a dipolar aprotic solvent such as N,N-dimethylformamide, N,N-dimethylacetamide, N-ethylpyrrolidin-2-one or dimethylsulphoxide. The reaction is conveniently carried out at a temperature in the range of, for example, 10 to 250° C., preferably in the range of 50–150° C.

The preparation of compounds of formula (VII) from compounds of formula (VIII) is also described by Ugi, I., et al., Liebigs Ann. Chem. 641 (1961) 63–70.

(B) Another preferred method for the preparation of compounds of the formula I is the reaction of a compound of the formula (V) with hydroxylamine.

This reaction typically involves a two-step one-pot procedure. In the first step, the carboxylate of the formula (V) becomes activated. This reaction is carried out in an inert solvent or diluent, for example, in dichloromethane, dioxane, or tetrahydrofurane, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. "Methoden der organischen Chemie (Houben-Weyl)", Vol. XV/1 and XV/2 are also applicable.

(C) A third preferred method for the production of compounds of the formula (I) involves the reaction of compounds of the formula (X)

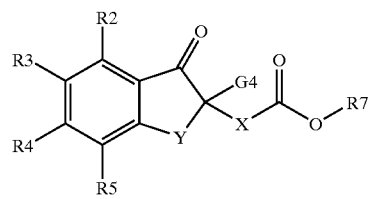

(X)

wherein X, Y, R2, R3, R4 and R5 have the meaning defined hereinbefore and G4 is hydrogen or a (1-4C)alkyl group or COOt.butoxy and R7 is a (1-4C)alkyl group, preferably a methyl or ethyl group, with hydroxylamine in the presence of a suitable base. The reaction is carried out in an inert solvent or diluent such as methanol or ethanol at temperatures between 0° C. and 100° C., conveniently at or near ambient temperature, and at a pH between 10 and 12. A suitable base is, for example, an alcoholate, for example, sodium methylate. Compounds of formula (X) are prepared in an analogous manner to that described for compounds of formula (VII).

The invention will now be illustrated in the following non-limiting examples in which, unless otherwise stated:
(i) evaporations were carried out by rotary evaporation in vacuo and work-up procedures were carried out after removal of residual solids such as drying agents by filtration;
(ii) operations were carried out at ambient temperature, that is in the range 18–25° C. and under an atmosphere of an inert gas such as nitrogen;
(iii) column chromatography (by the flash procedure) and high pressure liquid chromatography (HPLC) were performed on Merck Kieselgel silica or Merck Lichroprep™ RP-18 reversed-phase silica obtained from E. Merck, Darmstadt, Germany;
(iv) yields are given for illustration only and are not necessarily the maximum attainable;
(v) melting points were determined using a Büchi 510 melting point apparatus.
(vi) the structures of the end-products of the formula I were confirmed by nuclear (generally proton) magnetic resonance (NMR) and mass spectral techniques;
(vii) intermediates were not generally fully characterized and purity was assessed by thin layer chromatography (TLC);
(viii) the following abbreviations have been used:
DMF, N,N-dimethylformamide;
DMSO, dimethylsulphoxide;
THF, tetrahydrofurane;
MeOH, methanol;
HCl, hydrochloric acid;
NaH, sodium hydride
$CH_2Cl_2$, dichloromethane;
$H_2SO_4$, sulphuric acid
sat., saturated
sol., solution
rt, room temperature

EXAMPLE 1

5-(1-oxo-1,2,3,4-tetrahydro-naphthalen-2-yl)-pentanoic acid hydroxamide (1d)

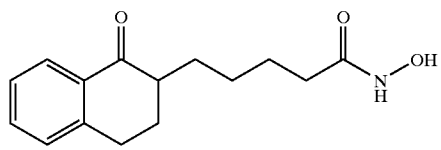

To a solution of 5.0 g (22.9 mmol) 1-oxo-1,2,3,4-tetrahydro-naphthalene-2-carboxylic acid ethyl ester (1a) (Pradeep, K., and Saravanan, K., Tetrahedron 54 (1998) 2161–2168) and 5.79 g ethyl-5-bromo-pentanoate (27.7 mmol) in 10 mL ethanol at reflux is added a freshly prepared solution of 0.53 g sodium in 15 mL ethanol. After 10 h at reflux enough water is added for the precipitate to dissolve. The solvent is evaporated, the residue is dissolved in a solution of 3.85 g KOH in 7 mL MeOH and 5 mL $H_2O$ and refluxed for another 10 h. After cooling the solution is poured into 25 mL ice-cold 4N HCl and extracted with $CH_2Cl_2$. Evaporation of the solvent leaves a residue of crude 5-(1-oxo-1,2,3,4-tetrahydro-naphthalen-2-yl)-pentanoic acid (1b) which is dissolved in 100 mL MeOH. A few drops of $H_2SO_4$ are added and the solution is refluxed over night. After addition of some sodiumbicarbonate-solution the solvent is evaporated and the residue is subjected to column-chromatography yielding 1.9 g methyl-(5-(1-oxo-1,2,3,4-tetrahydro-naphthalen-2-yl)-pentanoate) (1c). To a solution of 1.6 g (23 mmol) hydroxylamine hydrochloride in 40 mL MeOH is added 15 mL of a solution of 0.8 g (35 mmol) of sodium in 30 mL of MeOH. To this, a solution of 3.0 g (11.5 mmol) methyl-(5-(1-oxo-1,2,3,4-tetrahydro-naphthalen-2-yl)-pentanoate) (1c) in 20 mL MeOH is added, followed by the remaining 15 mL of the sodium methylate solution. After stirring for 6 h at rt the solvent is evaporated, acidified with 2N HCl and extracted with $CH_2Cl_2$. After evaporation the residue is purified by column-chromatography yielding 2.2 g of the title compound as an oil, MS (APCI): 260.1 (M–1).

EXAMPLE 2

5-(6-methoxy-1-oxo-1,2,3,4-tetrahydro-naphthalen-2-yl)-pentanoic acid hydroxyamide (2d)

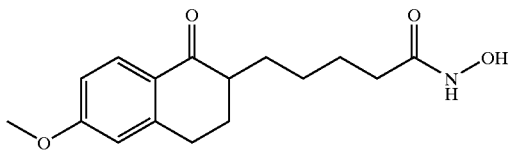

5-(6-methoxy-1-oxo-1,2,3,4-tetrahydro-naphthalen-2-yl)-pentanoic acid (2b) is prepared from 6-methoxy-1-oxo-1,2,3,4-tetrahydro-naphthalene-2-carboxylic acid ethyl ester (2a) (Basu, B., et al., Synth. Commun., 11, 10, 1981, 803–810) in an analogous manner to that described for 1b in example 1. 6.6 g (24.3 mmol) 1b are dissolved in 140 mL of $CH_2Cl_2$. To this solution is added sequentially 3.3 mL triethylamine, 6.9 g bis-(2-oxo-3-oxazolidinyl)-phosphorylchlorid, 3.0 g O-benzylhydroxylamine and another 10.2 mL triethylamine. After stirring over night the solution is washed with 2N HCl, then sat. NaCl sol., and evaporated. On treating with diethylether, 8.5 g 5-(6-Methoxy-1-oxo-1,2,3,4-tetrahydro-naphthalen-2-yl)-pentanoic acid benzyloxy-amide (2c) is obtained as bright crystals. Hydrogenation of 0.5 g of 2c in Methanol with $Pd/BaCO_3/Pb$ as a catalyst yields, after evaporation and treating with diethylether, 0.3 g of the title compound, MP 118–120° C.

The enantiomers of 2d were separated by semipreparative HPLC using a Chiracel OJ-R and water/methanol as the mobile phase. Purity was determined by analytical HPLC (Chiracel OJ-R column [15 cm, 4.6 mm, particle size 5 µm] using water 35/ methanol 65 v/v at a flow rate of 0.6 ml/min, injection of 5 µl-samples). Retention time and % ee of each enantiomer was 17.53 min (91% ee) and 21.96 min (84% ee), respectively.

EXAMPLE 3

6-(6-chloro-1-oxo-1,2,3,4-tetrahydro-naphthalen-2-yl)-hexanoic acid hydroxyamide (3c)

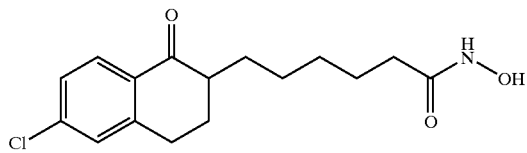

6-(6-Chloro-1-oxo-1,2,3,4-tetrahydro-naphthalen-2-yl)-hexanoic acid (3b) is prepared from 6-chloro-1-oxo-1,2,3,4-tetrahydro-naphthalene-2-carboxylic acid ethyl ester (3a) (WO 98/54350) in an analogous manner to that described for 1b in example 1 using ethyl-6-bromo-hexanoate instead of ethyl-6-bromo-hexanoate. To 1.6 g of 3b in 20 mL of $CH_2Cl_2$ 3.7 mL triethylamine and 1.5 g 9 g bis-(2-oxo-3-oxazolidinyl)-phosphorylchlorid are added. After stirring for 30 min, 1.7 g O-tritylhydroxylamine is added and stirring is continued overnight. The solution is extracted with 2N HCl and evaporated, yielding 2.9 g of an oil. This is redissolved in 20 mL $CH_2Cl_2$ and 10 mL of trifluoroacetic acid and stirred for 4 h. After washing with water and evaporation of the solvent, the crude product is subjected to column-chromatography yielding 60 mg of the title compound as an oil, MS (APCI): 308.1 (M−1).

EXAMPLE 4

6-(2-methyl-1-oxo-1,2,3,4-tetrahydro-naphthalen-2-yl)-hexanoic acid hydroxyamide (4c)

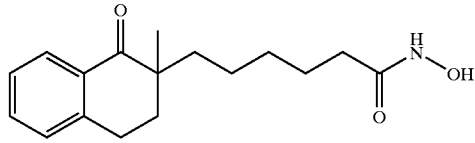

To a suspension of 0.7 g NaH in 40 mL of dry THF are added 4.0 g 2-methyl-1-tetralon in 20 mL of THF. After stirring for 30 min, 5.5 g ethyl-6-bromo-hexanoate in 10 mL of THF are added and the mixture is refluxed for 6 h. After evaporation of the solvent the residue is dissolved in a solution of 4.16 g potassium hydroxide in 50 mL of MeOH and 20 mL of $H_2O$ and heated to reflux over night. After evaporation of the MeOH, the aqueous phase is extracted with ethylacetate, acidified with 2N HCl, and extracted again with ethylacetate. This second extract is evaporated yielding 4.2 g of crude 6-(2-methyl-1-oxo-1,2,3,4-tetrahydro-naphthalen-2-yl)-hexanoic acid (4a). In an analogous manner to that described for the conversion of 3b to 3c in example 3, 4a is converted to the title compound 4c. 4c is an oil MS (APCI): 288.1 (M−1). The enantiomers of 4c were separated by semipreparative HPLC using a Chiracel OJ-R and water/methanol as the mobile phase. Purity was determined by analytical HPLC (Chiracel OJ-R column [15 cm, 4.6 mm, particle size 5 µm] using water 40/ methanol 60 v/v at a flow rate of 0.6 ml/min, injection of 10 µl-samples). Retention time and % ee of each enantiomer was 16.75 min (100% ee) and 20.25 min (87% ee), respectively.

EXAMPLE 5

6-(1-oxo-1,2,3,4-tetrahydro-naphthalen-2-yl)-hexanoic acid hydroxyamide (5c)

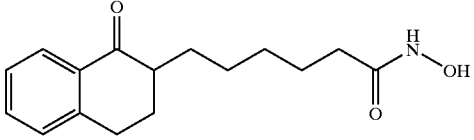

6-(1-oxo-1,2,3,4-tetrahydro-naphthalen-2-yl)-hexanoic acid hydroxyamide (5a) is prepared from 1-oxo-1,2,3,4-tetrahydro-naphthalene-2-carboxylic acid ethyl ester (1a) in an analogous manner to that described for the conversion of 3a to 3c in example 3. Yield in the last step is 10%, MS (APCI): 274.1 (M−1).

EXAMPLE 6

5-(2-Methyl-1-oxo-1,2,3,4-tetrahydro-naphthalen-2-yl)-pentanoic acid hydroxyamide (6b)

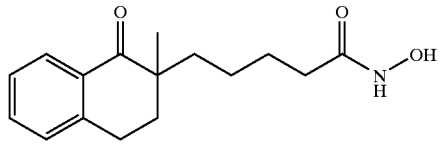

To a suspension of 0.86 g NaH in 40 mL of dry THF are added 5.0 g 2-methyl-1-tetralon in 20 mL of THF. After stirring for 30 min, 7.5 g ethyl-5-bromo-pentanoate in 20 mL of THF are added and the mixture is refluxed for 6 h. The cooled mixture is poured into water and extracted with ethylacetate. The extract is evaporated yielding crude ethyl-5-(2-Methyl-1-oxo-1,2,3,4-tetrahydro-naphthalen-2-yl)-pentanoate (6a) which is purified by column chromatography, yielding 3.6 g of pure 6a. 6a is converted to 6b in an analogous manner to that described for the conversion of 1c to 1d in example 1. 6b was obtained as an oil, MS (APCI): 274.1 (M−1).

The enantiomers of 6b were separated by semipreparative HPLC using a Chiracel OJ-R and water/methanol as the mobile Phase. Purity was determined by analytical HPLC (Chiracel OJ-R column [15 cm, 4.6 mm, particle size 5 µm] using water 40/ methanol 60 v/v at a flow rate of 0.6 ml/min, injection of 10 µl-samples). Retention time and % ee of each enantiomer was 11.48 min (100% ee) and 13.86 min (95% ee), respectively.

EXAMPLE 7

6-(2-methyl-1-oxo-1,2,3,4-tetrahydro-naphthalen-2-yl)-hex-5-enoic acid hydroxyamide (7c)

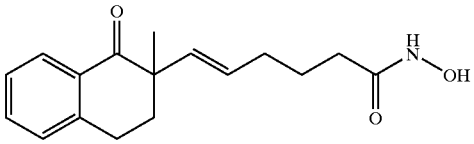

To 1.55 mL diisopropylamine in 40 mL THF is added a solution of 4.36 mL n-butyllithium (2.5M) in hexane at −78° C. After 10 min, 1.63 g 2-methyl-1-tetralone in 5 mL THF is added, and the solution is stirred for 50 min. Then, 1.60 g 6-oxo-hexanoic acid methyl ester in 5 mL THF is added dropwise, and stirring is continued for 15 min. After that, the cooling bath is removed and the mixture allowed to reach rt.

Conc. ammoniachloride sol is added, and extracted with ethylacetate. After evaporation the residue is purified by column chromatography yielding 0.8 g 6-hydroxy-6-(2-methyl-1-oxo-1,2,3,4-tetrahydro-naphtalen-2-yl)-hexanoic acid methyl ester (7a). 2.5 g of this alcohol 8a is dissolved in 50 mL dichloromethane and 2.27 mL triethylamine is added. After cooling to 0° C., 2.86 g methanesulfonic acid anhydride in 20 mL dichloromethane is added dropwise. After complete addition, the cooling bath is removed and stirring continued over night. The solution is washed with 2N HCl and water, separated, dried and evaporated. The crude product and 1.6 g 1,8-diazabicyclo[5.4.0]undecen-7-en (DBU) is dissolved in 60 mL toluene an heated to reflux for 24 h. The mixture is poured on 2N HCl and extracted with dichloromethane. After evaporaton and column chromatography 0.6 g 6-(2-methyl-1-oxo-1,2,3,4-tetrahydro-naphtalen-2-yl)-hex-5-enoic acid methyl ester (7b) is obtained. 7b is converted to 7c in an analogous manner to that described for the conversion of 1c to 1d in example 1. 7c was obtained as an oil, MS (APCI): 286.1 (M−1).

EXAMPLE 8

5-(5-methoxy-1-oxo-1,2,3,4-tetrahydro-naphthalen-2-yl)-hexanoic acid hydroxamide (8f)

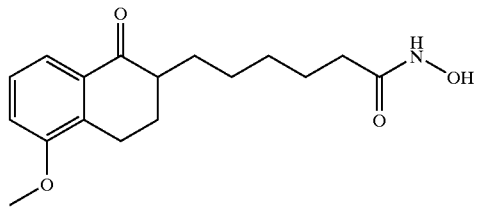

5-methoxy-1-oxo-1,2,3,4-tetrahydro-naphthalene-2-carboxylic acid ethyl ester (2,34 g; 8a) (Genet, J. P., et al., Tetrahedron Lett. 35 (1994) 4559–4562) is treated with ethyl-6-bromo-hexanoate in a analogues way to that described for the conversion of 3a in example 3. This resulted in a mixture of 6-(5-methoxy-1-oxo-1,2,3,4-tetrahydro-naphthalen-2-yl)-hexanoic acid (8b) and 2-(5-Carboxy-pentyl)-5-methoxy-1-oxo-1,2,3,4-tetrahydro-naphtalene-2-carboxylic acid ethyl ester (8c) in a ratio of approximately 1:1. This mixture of acids is treated with O-benzylhydroxylamine in a similar way as described for the conversion of 2b into 2c in example 2. The crude product is subjected to column chromatography yielding an inseparable mixture of 2-(5-benzyloxycarbamoyl-pentyl)-5-methoxy-1-oxo-1,2,3,4-tetrahydro-naphtalene-2-carboxyclic acid ethyl ester (8d) and 6-(5-methoxy-1-oxo-1,2,3,4-tetrahydro-naphtalen-2-yl)-hexanoic acid benzyloxy-amide (8e). This mixture is hydrogenated in methanol with Pd/C/BaSO₄ as a catalyst.

The resulting raw product is purified by LC/MS. Collection of the fraction with a mass of 305 yields the title compound, MS (APCI): 306.1 (M+1).

EXAMPLE 9
2-(5-hydroxycarbamoyl-pentyl)-5-methoxy-1-oxo-1,2,3,4-tetrahydro-naphtalene-2-carboxyclic acid ethyl ester (9a).

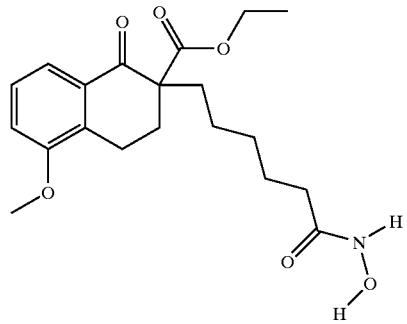

From the same LC/MS separation as described in example 8, a fraction with a mass of 377 was obtained, yielding the title compound, MS (APCI): 378.3 (M+1).

EXAMPLE 10
2-(7-Hydroxycarbamoyl-heptyl)-5,7-dimethyl-1-oxo-1,2,3,4-tetrahydro-naphtalene-2-carboxylic acid ethyl ester (10d)

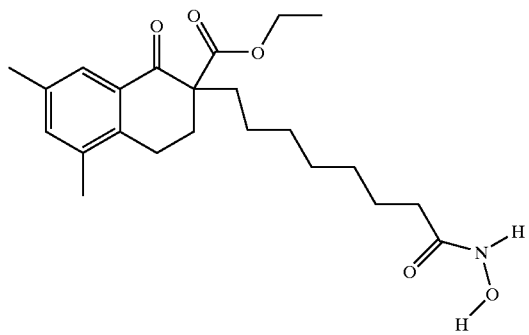

5,7-dimethyl-1-oxo-1,2,3,4-tetrahydro-naphthalene-2-carboxylic acid ethyl ester (10a) was prepared from 5,7-dimethyl-1-tetralone in the usual way. To a solution of 3.5 g 10a and 4.5 g methyl-8-bromo-octanonoat in 30 mL ethanol at reflux is added a freshly prepared solution of 0.35 g sodium in 15 mL ethanol. After 15 h at reflux the ethanol is evaporated, and dichloromethane and water are added. After separation and column chromatography, 4.0 g of a yellow oil is obtained. This residue is dissolved in a solution of 690 mg KOH in 10 mL of water and 10 mL of MeOH and refluxed for another 13 h. After cooling the solution is acidified with 2N HCl and extracted with CH₂Cl₂. Evaporation of the solvent leaves a residue of crude 2-(7-carboxy-heptyl)-5,7-dimethyl-1-oxo-1,2,3,4-tetrahydro-naphtalene-2-carboxylic acid ethyl ester. (10b) which is purified by column chromatography, yielding 1.2 g 10b. 630 mg of acid 10b are dissolved in 10 mL of diethylether and 0.3 mL N-methylmorpholine and 0.33 mL isobutyl chloroformate are added, followed by 270 mg O-benzylhydroxylamine. Usual workup yields 600 mg (71%) of 2-(7-benzyloxycarbamoyl-heptyl)-5,7-dimethyl-1-oxo-1,2,3,4-tetrahydro-naphtalene-2-carboxylic acid ethyl ester. (10c). 10c is converted to the title compound in a manner similar to that described for the conversion of 2c into 2d in example 2. MS (APCI): 402.52 (M−1).

EXAMPLE 11

In an analogous manner to that described in the examples 1–10 and using known methods as described in the literature (e.g. in standard works such as Houben-Weyl, "Methoden der Organischen Chemie, Georg Thieme Verlag", Stuttgart; Organic Reactions, John Wiley & Sons, Inc., New York) the following compounds are prepared:
a) 5-(6,7-dimethoxy-1-oxo-1,2,3,4-tetrahydro-naphthalen-2-yl)-pentanoic acid hydroxyamide
b) 6-(6-dimethylamino-2-methyl-1-oxo-1,2,3,4-tetrahydro-naphthalen-2-yl)-hexanoic acid hydroxyamide
c) 6-(6,7-dimethoxy-2-methyl-1-oxo-1,2,3,4-tetrahydro-naphthalen-2-yl)-hexanoic acid hydroxyamide
d) 5-(6,7-dimethoxy-2-methyl-1-oxo-1,2,3,4-tetrahydro-naphthalen-2-yl)-pentanoic acid hydroxyamide
e) 6-(6-diethylamino-2-methyl-1-oxo-1,2,3,4-tetrahydro-naphthalen-2-yl)-hexanoic acid hydroxyamide
f) 6-(2-methyl-1-oxo-6-pyrrolidin-1-yl-1,2,3,4-tetrahydro-naphthalen-2-yl)-hexanoic acid hydroxyamide
g) 6-(2-methyl-1-oxo-6-piperidin-1-yl-1,2,3,4-tetrahydro-naphthalen-2-yl)-hexanoic acid hydroxyamide
h) 6-(2-methyl-1-oxo-6-phenyl-1,2,3,4-tetrahydro-naphthalen-2-yl)-hexanoic acid hydroxyamide
i) 6-(6-bromo-2-methyl-1-oxo-1,2,3,4-tetrahydro-naphthalen-2-yl)-hexanoic acid hydroxyamide
j) 5-(7-methoxy-1-oxo-1,2,3,4-tetrahydro-naphthalen-2-yl)-pentanoic acid hydroxyamide
k) 5-(5-methoxy-1-oxo-1,2,3,4-tetrahydro-naphthalen-2-yl)-pentanoic acid hydroxyamide
l) 5-(5,7-dimethyl-1-oxo-1,2,3,4-tetrahydro-naphthalen-2-yl)-pentanoic acid hydroxyamide
m) 6-(2-methyl-1-oxo-6-pyridin-2-yl-1,2,3,4-tetrahydro-naphthalen-2-yl)-hexanoic acid hydroxyamide
n) 6-(2-methyl-1-oxo-6-pyridin-3-yl-1,2,3,4-tetrahydro-naphthalen-2-yl)-hexanoic acid hydroxyamide
o) 6-(2-methyl-1-oxo-6-pyridin-4-yl-1,2,3,4-tetrahydro-naphthalen-2-yl)-hexanoic acid hydroxyamide
p) 5-(7-dimethylamino-1-oxo-1,2,3,4-tetrahydro-naphthalen-2-yl)-pentanoic acid hydroxyamide
q) 5-(7-amino-1-oxo-1,2,3,4-tetrahydro-naphthalen-2-yl)-pentanoic acid hydroxyamide
r) 6-(2,6-dimethyl-1-oxo-1,2,3,4-tetrahydro-naphthalen-2-yl)-hexanoic acid hydroxyamide
s) 5-(2-ethyl-1-oxo-1,2,3,4-tetrahydro-naphthalen-2-yl)-pentanoic acid hydroxyamide
t) 6-(2,5,8-trimethyl-1-oxo-1,2,3,4-tetrahydro-naphthalen-2-yl)-hexanoic acid hydroxyamide
u) 5-(6,7-dimethoxy-1-oxo-1,2,3,4-tetrahydro-naphthalen-2-yl)-pentanoic acid hydroxyamide
v) 2-(4-hydroxycarbamoyl-butyl)-5,7-dimethyl-1-oxo-1,2,3,4-tetrahydro-naphthalene-2-carboxylic acid methyl ester
w) 2-(5-hydroxycarbamoyl-pentyl)-6-methyl-1-oxo-1,2,3,4-tetrahydro-naphthalene-2-carboxylic acid methyl ester
x) 2-(4-hydroxycarbamoyl-butyl)-1-oxo-1,2,3,4-tetrahydro-naphthalene-2-carboxylic acid
y) 5-(7-dimethylamino-2-methyl-1-oxo-1,2,3,4-tetrahydro-naphthalen-2-yl)-2,2-dimethyl-pentanoic acid hydroxyamide
z) 2-methyl-5-(2-methyl-1-oxo-1,2,3,4-tetrahydro-naphthalen-2-yl)-pentanoic acid hydroxyamide
aa) 1-[3-(2-methyl-1-oxo-1,2,3,4-tetrahydro-naphthalen-2-yl)-propyl]-cyclopropanecarboxylic acid hydroxyamide
bb) 5-(2-methyl-1-oxo-1,2,3,4-tetrahydro-naphthalen-2-yl)-pent-4-enoic acid hydroxyamide
cc) 6-(7-Chloro-2-methyl-1-oxo-1,2,3,4-tetrahydro-naphthalen-2-yl)-hexanoic acid hydroxyamide
dd) 2-(5-hydroxycarbamoyl-pentyl)-5,7-dimethyl-1-oxo-1,2,3,4-tetrahydro-naphthalene-2-carboxylic acid ethyl ester.

EXAMPLE 12

Evaluation of inhibitory properties of the compounds of the invention.

To measure the HDAC inhibitory properties of the compounds of the invention a screening assay was established using an aminocoumarin derivative of an omega-acetylated lysine as substrate for the enzyme. This assay has been described in detail by Hoffmann, K., et al., Nucleic Acid Research 27 (1999) 2057–2058). Using the protocol described therein, the inhibitory effect of the new compounds was determined at a concentration of 10 nM. The observed inhibition rates for selected compounds are shown in Table 1:

| Title compound of example No. | 8 | 4 | 2 | 7 | 9 | 10 |
|---|---|---|---|---|---|---|
| Inhibitory effect at 10 nM in % | 72 | 71 | 64 | 60 | 57 | 55 |

In the same assay, suberanilohydroxamic acid (SAHA) (referenced on page 2) showed an inhibitory effect of 42% at 10 nM.

EXAMPLE 13

| | Tablet formulation | |
|---|---|---|
| Item | Ingredients | mg/Tablet |
| 1 | Compound 2d | 25 100 |
| 2 | Anhydrous Lactose | 73 35 |
| 3 | Croscarmellose Sodium | 6 8 |
| 4 | Povidone K30 | 5 6 |
| 5 | Magnesium Stearate | 1 1 |
| | Total Weight | 140 150 |

Compound 2d is described in Example 2.
Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

EXAMPLE 14

| | Capsule formulation | |
|---|---|---|
| Item | Ingredients | mg/Capsule |
| 1 | Compound 2d | 50 100 |
| 2 | Anhydrous Lactose | 123 148 |
| 3 | Corn Starch | 35 40 |
| 4 | Talc | 15 10 |
| 5 | Magnesium Stearate | 2 2 |
| | Total Fill Weight | 225 300 |

Procedure:
1. Mix Items 1, 2 and 3 in a suitable mixer for 15 minutes.
2. Add Items 4 & 5 and mix for 3 minutes.
3. Fill into a suitable capsule.

What is claimed is:

1. A compound selected from compounds of formula I

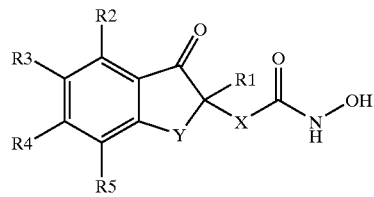

wherein:
R1 is selected from hydrogen, (1-4C)alkyl, COOH, and COO(1-4C)alkyl;
R2, R3, R4, R5 are independently selected from hydrogen, a halogen atom, an (1-4C)alkyl-, trifluoromethyl-, hydroxy-, (1-4C)alkoxy-, aryloxy-, arylalkyloxy-, nitro-, amino-, (1-4C)alkylamino-, di[(1-4C)alkyl]-amino-, piperidino, morpholino, pyrrolidino, (1-4C)alkanoylamino-, an aryl group, and a heteroaryl group, or R2 and R3 together or R3 and R4 together or R4 and R5 together, respectively, can form an (1-3C)alkylenedioxy ring, or R2 and R3 together or R3 and R4 together or R4 and R5 together, respectively, can form an (3-5C)alkylene chain;
Y is —CH2—CH2—;
X is an alkylene chain of 4 to 10 carbon atoms which can be saturated or unsaturated with one or two double bonds or one or two triple bonds or a one double and one triple bond, and which can be branched or unbranched or interrupted by a (3-7C) cycloalkyl ring;
and pharmaceutically acceptable salts thereof.

2. A compound according to claim 1 wherein R1 is selected from hydrogen, (1-4C) alkyl, and COOR in which R is hydrogen or (1-4C) alkyl.

3. A compound according to claim 1 wherein R2, R3, R4 and R5 are independently hydrogen or three of them are hydrogen or R2 and R5 are hydrogen.

4. A compound according to claim 1 wherein X is selected from —(CH$_2$)$_n$— and —CH=CH—(CH$_2$)$_{n-2}$—, in which n is an integer from 3 to 7.

5. A compound according to claim 1 wherein X is selected from —(CH$_2$)$_{n-1}$—CH(CH$_3$)—, —(CH$_2$)$_{n-1}$—C(CH$_3$)$_2$— and —(CH$_2$)$_{n-1}$—C(—CH$_2$—CH$_2$—)— in which n is an integer from 3 to 7.

6. A compound according to claim 1, selected from the group consisting of
5-(1-oxo-1,2,3,4-tetrahydro-naphthalen-2-yl)-pentanoic acid hydroxamide;
5-(6-methoxy-1-oxo-1,2,3,4-tetrahydro-naphthalen-2-yl)-pentanoic acid hydroxyamide;
6-(6-chloro-1-oxo-1,2,3,4-tetrahydro-naphthalen-2-yl)-hexanoic acid hydroxyamide;
6-(2-methyl-1-oxo-1,2,3,4-tetrahydro-naphthalen-2-yl)-hexanoic acid hydroxyamide;
6-(1-oxo-1,2,3,4-tetrahydro-naphthalen-2-yl)-hexanoic acid hydroxyamide;
5-(2-Methyl-1-oxo-1,2,3,4-tetrahydro-naphthalen-2-yl)-pentanoic acid hydroxyamide;
6-(2-methyl-1-oxo-1,2,3,4-tetrahydro-naphthalen-2-yl)-hex-5-enoic acid hydroxyamide;
5-(5-methoxy-1-oxo-1,2,3,4-tetrahydro-naphthalen-2-yl)-hexanoic acid hydroxamide;
2-(5-hydroxycarbamoyl-pentyl)-5-methoxy-1-oxo-1,2,3,4-tetrahydro-naphtalene-2-carboxyclic acid ethyl ester;
2-(7-Hydroxycarbamoyl-heptyl)-5,7-dimethyl-1-oxo-1,2,3,4-tetrahydro-naphtalene-2-carboxylic acid ethyl ester; and
6-(7-Chloro-2-methyl-1-oxo-1,2,3,4-tetrahydro-naphthalen-2-yl)-hexanoic acid hydroxyamide.

7. A process for making a compound of formula I

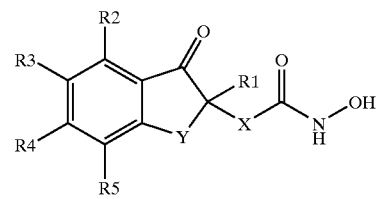

wherein:
R1 is selected from hydrogen, (1-4C)alkyl, COOH, and COO(1-4C)alkyl;
R2, R3, R4, R5 are independently selected from hydrogen, a halogen atom, an (1-4C)alkyl-, trifluoromethyl-, hydroxy-, (1-4C)alkoxy-, aryloxy-, arylalkyloxy-, nitro-, amino-, (1-4C)alkylamino-, di[(1-4C)alkyl]-amino-, piperidino, morpholino, pyrrolidino, (1-4C)alkanoylamino-, an aryl group, and a heteroaryl group, or R2 and R3 together or R3 and R4 together or R4 and R5 together, respectively, can form an (1-3C)alkylenedioxy ring, or R2 and R3 together or R3 and R4 together or R4 and R5 together, respectively, can form an (3-5C)alkylene chain;
Y is —CH2—CH2—;
X is an alkylene chain of 4 to 10 carbon atoms which can be saturated or unsaturated with one or two double bonds or one or two triple bonds or one double and one triple bond, and which can be branched or unbranched or interrupted by a (3-7C) cycloalkyl ring;
and pharmaceutically acceptable salts thereof,
by reacting a compound of formula III

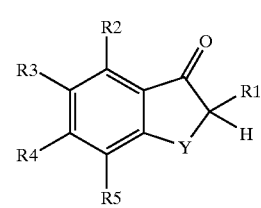

with a compound of formula IV

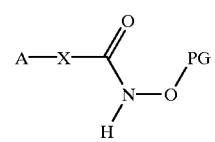

wherein
A is a displaceable group and PG is a protecting group.

8. A pharmaceutical composition comprising a compound according to claim 1 in admixture with at least one pharmaceutically acceptable excipient.

* * * * *